(12) United States Patent
Kathe et al.

(10) Patent No.: US 9,023,657 B2
(45) Date of Patent: May 5, 2015

(54) METHOD FOR OPERATING AN ANALYTICAL APPARATUS

(75) Inventors: Ulrich Kathe, Ludwigsburg (DE); Oliver Bettmann, Russelsheim (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 844 days.

(21) Appl. No.: 13/258,111

(22) PCT Filed: Mar. 15, 2010

(86) PCT No.: PCT/EP2010/053267
§ 371 (c)(1),
(2), (4) Date: Sep. 21, 2011

(87) PCT Pub. No.: WO2010/108802
PCT Pub. Date: Sep. 30, 2010

(65) Prior Publication Data
US 2012/0015447 A1    Jan. 19, 2012

(30) Foreign Application Priority Data
Mar. 25, 2009   (DE) .......................... 10 2009 001 861

(51) Int. Cl.
*G01N 1/00* (2006.01)
*G01N 33/18* (2006.01)
*G01N 35/00* (2006.01)

(52) U.S. Cl.
CPC ...... *G01N 33/1846* (2013.01); *G01N 35/00613* (2013.01); *G01N 35/00712* (2013.01); *G01N 2035/00643* (2013.01); *G01N 35/00623* (2013.01); *G01N 35/00693* (2013.01); *G01N 35/00594* (2013.01)

(58) Field of Classification Search
CPC ................... G01N 33/1846; G01N 35/00594; G01N 35/00623; G01N 35/00613; G01N 35/00693; G01N 35/00712; G01N 2035/00643
USPC ......................................................... 436/180
See application file for complete search history.

(56) References Cited

U.S. PATENT DOCUMENTS

| | | | | |
|---|---|---|---|---|
| 3,657,919 A | * | 4/1972 | Brown | ........................... 73/1.16 |
| 5,637,787 A | | 6/1997 | Fukushima et al. | |
| 5,783,740 A | | 7/1998 | Tawarayama et al. | |
| 6,302,130 B1 | * | 10/2001 | Ohmi et al. | ...................... 137/14 |
| 2005/0257595 A1 | * | 11/2005 | Lewis | ............................. 73/1.16 |
| 2009/0171502 A1 | * | 7/2009 | Freidin | ......................... 700/240 |
| 2010/0178706 A1 | * | 7/2010 | Bettmann et al. | ............. 436/114 |

FOREIGN PATENT DOCUMENTS

| | | |
|---|---|---|
| CN | 1059206 A | 4/1992 |
| DE | 2534260 | 2/1977 |
| DE | 9310077 | 2/1994 |
| DE | 4344441 | 7/1995 |
| DE | 19617910 | 11/1997 |
| DE | 102006058051 | 6/2008 |
| EP | 1167767 | 1/2002 |

OTHER PUBLICATIONS

Machine translation of DE 19617910, obtained by the examiner on Jul. 31, 2014 from <http://google.com/patents>.*
International Search Report in corresponding International Application No. PCT/EP2010/053267 dated Jun. 1, 2010.

* cited by examiner

*Primary Examiner* — Christopher A Hixson
(74) *Attorney, Agent, or Firm* — Bacon & Thomas, PLLC

(57) ABSTRACT

A method for operating an analytical apparatus for determining concentration of an analyte, especially an oxidizable substance, in a sample liquid, comprises the steps of: placing the analytical apparatus in maintenance operation; operating a metering system, which includes a pump, especially a peristaltic pump, and a supply line, for metering single volume units of a sample liquid from a source via the supply line into a reactor, wherein there exists in the reactor a temperature, which is greater than the boiling temperature of the sample liquid, so that a volume unit of the sample liquid metered into the reactor transforms at least partially into the gas phase following entry into the reactor, especially due to heat transfer from contact with a surface within the reactor, especially directly after contact with the surface within the reactor, and wherein a carrier gas is flowing through the reactor; registering at least one measuring transducer signal for detection of the transforming of the volume unit of the sample liquid into the gas phase, and deriving, with application of the measuring transducer signal, a signal correlated with an instantaneous operating state of the metering system.

19 Claims, 4 Drawing Sheets

Fig A

Fig 5
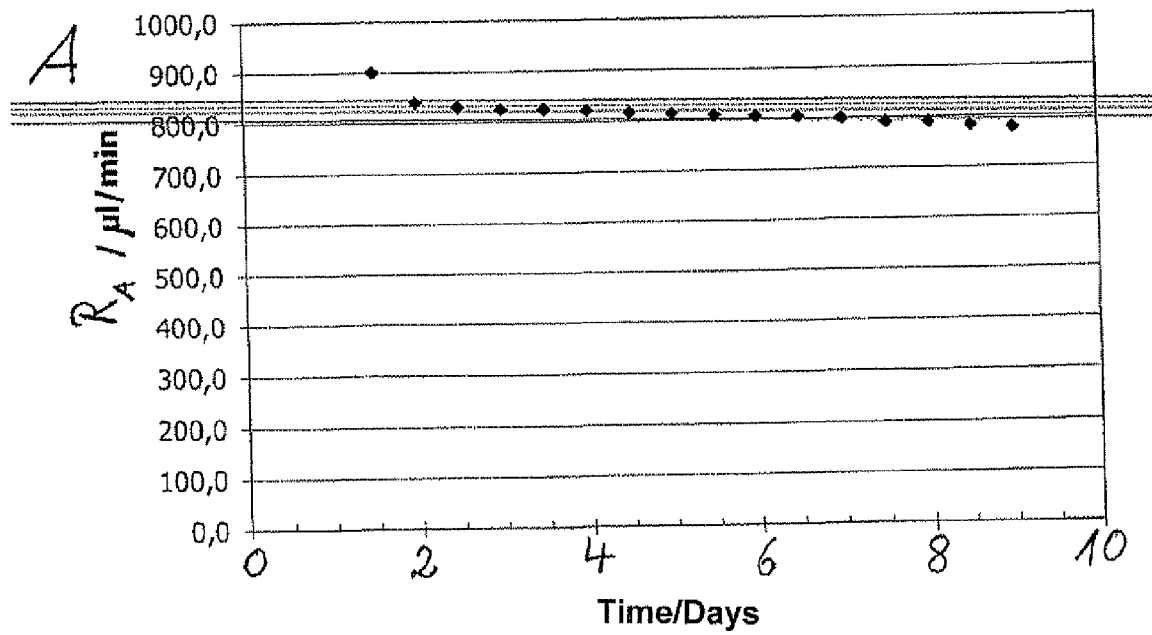
A
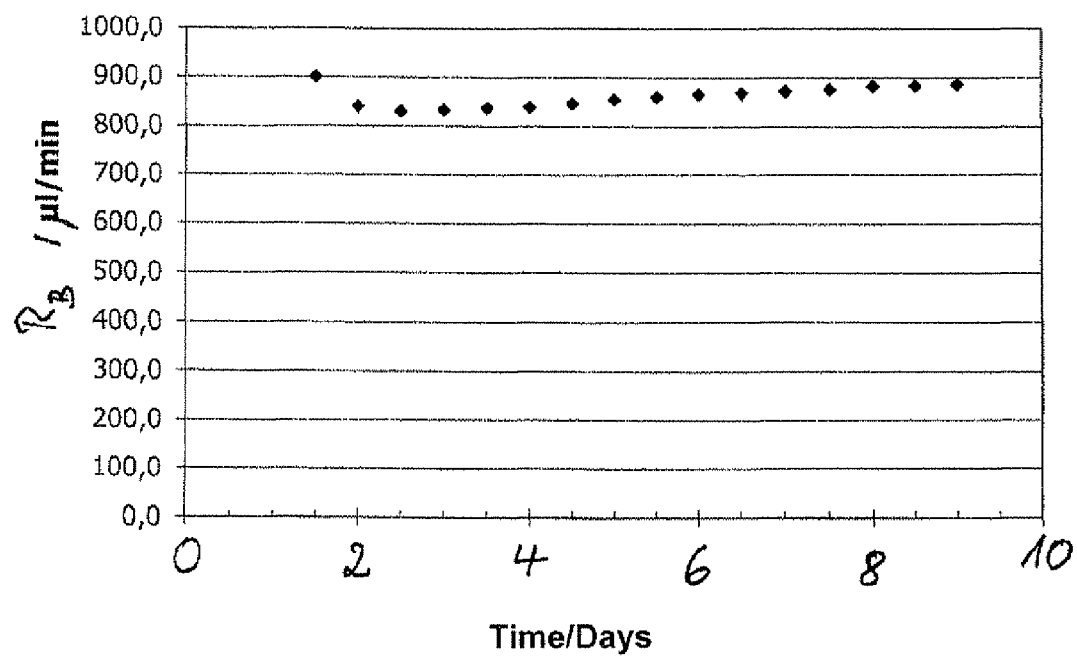
B

METHOD FOR OPERATING AN ANALYTICAL APPARATUS

TECHNICAL FIELD

The invention relates to a method for operating an analytical apparatus for determining concentration of an analyte, especially an oxidizable substance, in a sample liquid.

BACKGROUND DISCUSSION

Such an analyte can be, for example, in the waste water field, the total organic carbon, TOC (total organic carbon content), or the total bound nitrogen $TN_b$ (Total Nitrogen, total nitrogen content) in a water sample.

In the case of known methods for determining these parameters, a liquid sample of volume of, for example, some 100 s of µl is fed to a reactor in a high temperature decomposition system. In the reactor, which, for example, is provided by a high temperature reactor formed as a pyrolysis tube, the organic ingredients are thermally decomposed to $CO_2$ and the nitrogen containing ingredients to nitrogen oxide $NO_x$. The acronym $NO_x$ stands here for a mixture of nitrogen oxides with nitrogen in different degrees of oxidation, which, however, has NO as the main component. In the decomposition in the high temperature reactor, there arises a gas mixture, which besides $CO_2$ and $NO_x$ contains gaseous $H_2O$ and, in given cases, other pyrolysis- and reaction products of substances contained in the sample. The gas mixture is, with the assistance of a carrier gas (which, as a rule, also delivers the oxygen needed for the reaction) flowing permanently through the reactor, transported through a cooler having a water separator, a gas filter and an analytical unit. The amount of the occurring $CO_2$, or $NO_x$, is determined, for example, by infrared measurement or by chemiluminescent measurement, and, therefrom, the TOC-, or $TN_b$, content of the liquid sample determined.

The temperatures reigning in the reactor of the high temperature decomposition system lie during operation of the analytical apparatus significantly above the boiling point of the dosed sample liquid. In the case of TOC- or $TN_b$ determination, there rules in the interior of the reactor usually a temperature of about 650° C. up to 1300° C., depending on whether the decomposition of the sample is supported supplementally by a catalyst. In contact with the wall of the reactor or other surfaces present within the reactor, a liquid drop reaches, within a very short time, boiling temperature and, respectively, the reaction temperature required for the reaction with the oxygen contained in the carrier gas. A volume unit of the sample liquid, which e.g. can comprise one or more liquid drops dosed into the reactor transforms into the gas phase, consequently, directly after the dosing, by evaporation and/or by forming gaseous reaction products.

The described method can, on the one hand, be performed in continuous measurement operation. In such case, the sample liquid is metered in an ongoing manner with slow feed velocity, especially dropwise, into the reactor. The concentrations of the oxidation products of the analyte, e.g. the $CO_2$—, and $NO_x$, concentrations, respectively, in the carrier gas stream leaving the reactor are, to a first approximation, proportional to the concentration of the analyte in the sample liquid.

The method can, on the other hand, be performed in a batch fashion, in the case of which a volume unit, typically 100 to 1500 µl, of the sample liquid is decomposed in the reactor. The amount of oxidation product of the analyte contained in the carrier gas stream emerging from the reactor is correspondingly dependent both on the volume of the dosed sample liquid as well as also on the concentration of the analyte in the sample liquid.

Thus, it is clear that metering errors in the case of both methods enter proportionally the analysis result. The dosing of the sample liquid into an analytical apparatus of the initially described type occurs through one or more pumps comprising a supply line for supplying the sample liquid from a source into the reactor. Frequently in analyzers of the initially described field of the invention, one or more peristaltic pumps are used. In principle, also syringe pumps are applicable.

Syringe pumps work quite reproducibly and precisely. Their operation is, however, relatively expensive. Syringe pumps are furthermore not applicable in all fields of application for automatic analytical apparatuses. Especially, in the field of waste water analysis, due to deposition of particles present in the sample liquid or the crystallizing of solids, especially when such involve abrasive particle, the seals can be damaged, so that unsealed locations arise. Furthermore, through depositing of the particles on the inner wall of the supply line, despite pump power remaining equal, the feed rate, i.e. the volume of sample solution supplied per unit time into the reactor, can change.

A peristaltic pump is a squeeze pump, in the case of which the medium to be fed is pressed in the feed direction by external mechanical deformation, in the form of compressive stroking of a hose. Peristaltic pumps have especially the following advantages: They are inexpensive, simple to handle, the liquid comes only in contact with the hose, whereby corrosion is prevented, they are used over a large range of feed rates, namely between microliters per hour to liters per minute, and a plurality of hoses can be operated with one pump drive. Peristaltic pumps are, however, subject to the following constraints: The feed rate is not constant over the life cycle of the hose. The life cycle of a hose can be divided roughly into three phases, namely, first of all, a short break-in phase, in which the feed rate sinks moderately, second follows a long phase of relatively constant feed rate, and third, the feed rate declines toward the end of the life cycle, first slowly and then rapidly. Additionally, also in the case of a peristaltic pump, deposits on the inner wall of the hose can lead in places to cross sectional narrowing or even to clogging of the hose. Also damage to the hose, e.g. leaks, can a change the feed rate to such an extent that, eventually, the hose becomes unusable.

In order to prevent measurement errors from occurring due to a change of feed rate, different measures are used. The first position here is to be mentioned is the regular readjustment of the device using a standard solution. This readjustment requires time, however, and leads especially in the case of an analytical apparatus working in the continuous measuring mode to undesired interruptions.

Second, the supply line can be regularly cleaned, or, especially in the case of peristaltic pumps, preventitively replaced even after a relatively short time of use, e.g. when the tubes are still, with sufficiently high probability, located in the second phase of the life cycle with a stable pump behavior, even though the tubes could physically still provide service for a very long time. This means lastly an unnecessarily high maintenance effort and a waste of material.

Even in the case of regular adjustment, cleaning or in the case of early replacement of the supply line, especially the hose in the case of peristaltic pumps, it is still possible for defects, which occur due to leakages or unpredicted accreting or narrowing of the supply line, under circumstances not timely to be recognized, which leads to defective measurements.

EP 1 167 767 A1 discloses a method for monitoring an apparatus serving for producing a fluid flow for a sample collector, wherein the apparatus comprises a squeeze pump, especially a peristaltic pump, with a hose as supply line for the feed of a fluid. For monitoring the instantaneous operating state of the pump, especially the hose, in such case, an internal pressure reigning in an inlet region of the hose is measured. From pressure signals registered by means of a pressure measuring transducer arranged in an inlet region of the hose, especially the instantaneous volume flow can be ascertained. The monitoring of the pressure reigning in an inlet region of the hose gives, however, not necessarily reliable information concerning the state of the total supply line or concerning the sample volume actually metered into a vessel. In the case of an analytical apparatus of the initially described type, moreover, already low metering errors of a few drops, which corresponds to some 10 s of microliters, means, in the case of total sample volumes of 100 to 1500 µl, error in the one to two digit percent range in the analytical result. Such metering error can be caused already by a small change in the feed rate, which cannot be detected precisely enough by monitoring the liquid pressure in the supply line.

SUMMARY OF THE INVENTION

It is, therefore, an object of the present invention to provide a method for operating an analytical apparatus, which overcomes the disadvantages of the previously described method. Especially, a method for operating an analytical apparatus should be given, which assures reliable monitoring of the metering of the liquid sample, on the one hand, and a reliable measurement operation with high accuracy, on the other hand.

This object is achieved by a method for operating an analytical apparatus for determining concentration of an analyte, especially an oxidizable substance, in a sample liquid, wherein the method comprises steps as follows:
  placing the analytical apparatus in maintenance operation;
  operating a metering system, which includes a pump, especially a peristaltic pump, and a supply line, for metering single volume units of a sample liquid from a source via the supply line into a reactor;
  wherein there exists in the reactor a temperature, which is greater than the boiling temperature of the sample liquid, so that a volume unit of the sample liquid transforms at least partially into the gas phase directly after entry into the reactor, especially due to heat transfer from contact with a surface within the reactor, especially directly after contact with the surface within the reactor; and wherein a carrier gas is flowing through the reactor;
  registering at least one measuring transducer signal for detection of the transforming of the volume unit of the sample liquid into the gas phase, and
  deriving, with application of the measuring transducer signal, a signal correlated with an instantaneous operating state of the metering system.

Since the temperature of the reactor lies above the boiling temperature of the metered liquid, such transforms into the gas phase directly after entry into the reactor by evaporating and/or by forming gaseous reaction products. Especially in the case of contact with a surface within the reactor, for example, the inner wall of the reactor or a surface of an insert arranged in the reactor, heat transfer to the drops occurs especially rapidly, e.g. within less than 0.4 s, especially within less than 0.1 s. Detection of such a phase transformation is thus a suitable procedure, in order safely to detect that the metering system has fed a corresponding volume unit into the reactor. The signal of a measuring transducer, for example, a pressure- or a temperature sensor, suitable to detect this phase transformation can therefore be used to derive an instantaneous operating state of the metering system. Such a instantaneous operating state can concern the ability of the metering system to function. For example, the operating state can be one of complete failure of the metering system, which leads to the fact that no liquid is now being fed into the reactor, one of a cross sectional narrowing or complete clogging of the supply line, one of a change of the feeding power, especially the feed rate, or also one of the presence of a leak in the supply line.

Since, with application of the measuring transducer signal, a signal correlated with the instantaneous operating state is derived, a means is provided, based on which
  the ability of the metering system to function can be monitored, in order to detect, with high reliability, disturbances during metering of the liquid sample;
  an adjustment of the analytical apparatus can be performed, for example, by ascertaining a correction factor, with which in analytical operation the feed rate or the sample volume can be treated, in order to increase the accuracy of the analytical result;
  a precise contxdrol of the metering system can be performed, likewise in order to improve the accuracy of the analytical result.

The signal correlated with the instantaneous operating state can be, for example, a status signal, whose signal value tells, for example, whether sample liquid is being fed into the reactor. Furthermore, the signal correlated with the instantaneous operating state can have a signal value, from which information can be derive, such as, for example, the feeding power of the metering system, the liquid volume supplied in a certain unit of time, or similar data. Through the signal correlated with the instantaneous operating state or through a signal derived therefrom, a warning report can be released, which brings about, for example, maintenance measures such as a cleaning or a replacement of the supply line or a maintenance of the pump.

The signal can also represent a time span required for transporting sample liquid from the source into the reactor, or a value derived therefrom, such as, for example, the feed rate of the metering system. This is presented in more detail below.

It is advantageous, when the analytical apparatus, at time intervals during operation of the metering system, is repeatedly moved from analytical operation (in which, for example, as initially described, sample liquid is fed and the content of oxidizable ingredients in the sample liquid determined by measuring the content of oxidation products in the gas phase) into maintenance operation, and the signal correlated with the instantaneous operating state ascertained and stored in memory, especially together with information on the duration of operation of the metering system up to the point in time of the ascertaining of the signal.

A parameter especially more informative for monitoring the metering system is the time interval required, in order to feed a volume unit of the sample liquid from the source into the reactor. In order to determine this time interval, the method includes additional steps as follows:
  registering a first point in time ($t_o$), at which operation of the metering system is begun for metering single volume units of a sample liquid into the reactor;
  registering a second point in time ($t_1$), at which the transformation of a volume unit of the sample liquid metered into the reactor is detected based on the measuring transducer signal;

determining the time difference (Δt) between the first and second points in time as the signal correlated with the instantaneous operating state of the metering system.

In order to assure a defined starting point, at which the first point in time ($t_0$) is determined, the placing of the analytical apparatus into maintenance operation can comprise a step of removing sample liquid from the supply line, especially by having the pump supply sample liquid from the supply line back into the source, until gas from the supply line escapes into the source. This requires a pump, which is able to pump liquid in two opposed directions through the supply line.

In principle, for setting the second point in time, any type of detection of a phase transformation of a metered liquid volume into the gas phase can be used. If the liquid is metered dropwise, for example, the phase transformation of a first, however, also of a second, third, fourth, etc. drop can be used. In order to assure that an as small as possible error occurs in the volume determination of the metered liquid volume, it is helpful to choose an as early as possible point in time, wherein especially as second point in time ($t_1$) that point in time is registered, at which for the first time after registering the first point in time ($t_0$) a transformation of a volume unit metered into the reactor into the gas phase is detected.

In an advantageous embodiment, the measuring transducer signal is a pressure signal of a pressure measuring transducer.

In order to detect the transformation of a volume unit of the sample liquid metered into the reactor into the gas phase, it is advantageous to register a sequence of pressure signals, which are correlated with a pressure reigning within the reactor.

In order to register pressure signals, which are correlated with a pressure reigning within the reactor, the pressure measuring transducer is preferably arranged within the carrier gas stream. A pressure measuring transducer arranged within the carrier gas stream means a pressure measuring transducer, which is arranged at an any position along the flow path of the gas stream. Preferably, this position is selected to be outside of the reactor, since lower temperatures reign there than within the reactor. Flow resistances within the gas stream mean that pressure changes within the reactor are also detectable by a pressure measuring transducer arranged in the carrier gas stream outside the reactor, for example, by a pressure measuring transducer arranged within a supply line for delivery of the carrier gas stream into the reactor.

For detecting transformation of a metered volume unit of the sample liquid into the gas phase, for example, a current pressure signal ($P_n$) of the sequence is compared with a base pressure value ($P_{center}$), in order to ascertain a pressure change ($P_{delta}$) associated with the current pressure signal ($P_n$), and the pressure change ($P_{delta}$) is compared with a predetermined threshold value, and, on basis of a result of the comparison, it is registered, whether the pressure change ($P_{delta}$) corresponds to a pressure pulse effected by transformation of a volume unit metered into the reactor into the gas phase. The metering of a drop into the reactor is registered, for example, when the pressure change ($P_{delta}$) exceeds the predetermined threshold value.

The base pressure value ($P_{center}$) can be formed by average formation, especially by sliding average formation, by applying at least two pressure signals preceding the current pressure signal ($P_n$) in the sequence of pressure signals. For example, the base pressure value can be set at the beginning of the method at the pressure reigning before beginning the sample metering in the reactor. During registering pressure signals following one after another, the base pressure value can be adjusted by sliding average formation taking into consideration most up to date pressure signals of the sequence.

When the analytical apparatus, over the duration of operation of the metering system, is moved into maintenance operation between intervals, in which it is operated in normal analytical operation, offset, and, in each instance, a signal correlated with the operating state of the metering system, especially the previously described time difference Δt, is stored, a trend of the stored signals correlated with the operating state of the metering system, especially the time differences (Δt), can be determined and evaluated. Also for values derived from Δt, a trend can be ascertained and evaluated.

From the trend, a point in time for maintenance measures of the analytical apparatus, or especially the metering system, especially for cleaning or replacement of the supply line, can be derived. This can occur, for example, by comparison of a curve of the signals stored as a function of the duration of operation of the metering system with a stored model for the curve of these signals, for example, one based on experiential values. When a maintenance measure of the analytical apparatus or metering system has been performed, a reset function can be provided, which erases the previously registered signals correlated with the operating state of the apparatus, e.g. the described time differences Δt. In this way, only the signals registered since the last maintenance measure are taken into consideration in the evaluation of the trend.

Furthermore, based on the signal correlated with the operating state of the metering system, especially the time difference (Δt), an adjusting of the analytical apparatus can be performed.

In the case of adjusting the analytical apparatus, the trend of the time differences (Δt) ascertained in the course of the duration of operation of the analytical apparatus can be taken into consideration. For example, the trend can indicate which type the disturbance is, which, for example, leads to a change of the feed rate, or to a change of the internal volume of the supply line, from which, for example, one can know whether, in determining the analytical result, the internal volume of the supply line or the feed rate must be adjusted by means of a correction factor.

Instead of using the signal correlated with the operating state of the metering system for adjusting the analytical apparatus, the signal can also be used, in order to control the metering system.

BRIEF DESCRIPTION OF THE DRAWINGS

The invention will now be explained in greater detail based on the examples of embodiments illustrated in the drawing, the figures of which show as follows:

FIG. 5 shows two examples (A, B) for trend of the feed rate under different conditions.

DETAILED DISCUSSION IN CONJUNCTION WITH THE DRAWINGS

Figure 1:
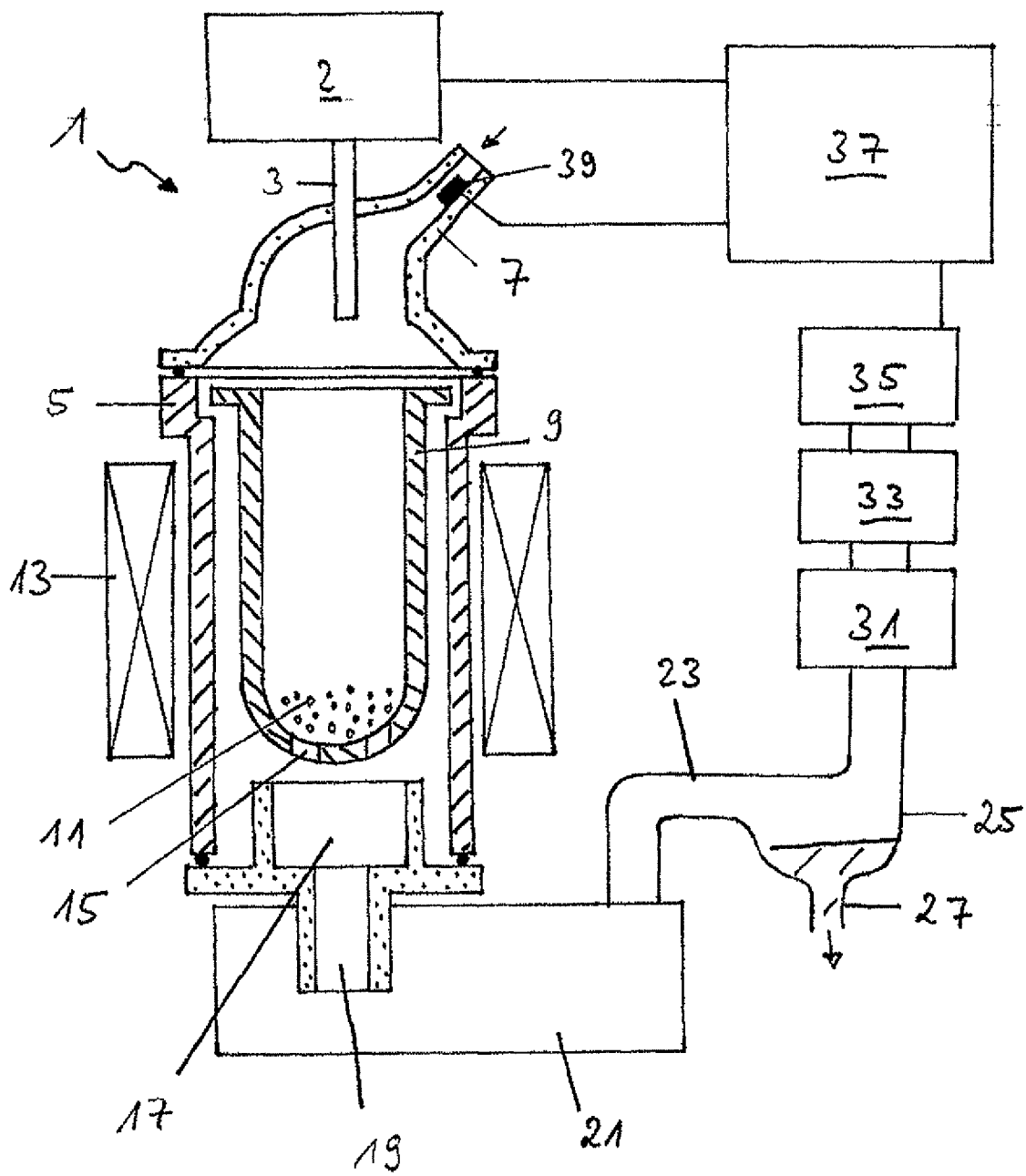
FIG. 1 is a schematic representation of an analytical apparatus for determining oxidizable contents in liquid samples.

In the case of the analytical apparatus 1 illustrated in FIG. 1 for determining, for example, TOC- or $TN_b$, content of a liquid sample, such is fed by a here only schematically illustrated metering system 2 via a drop cannula 3 to a reactor 5 embodied, for example, in the form of a pyrolysis tube. At the same time, the reactor 5 is fed via another delivery line 7 an oxygen containing carrier gas. The reactor 5 contains in the here shown example an insert 9, which contains a catalyst 11, which supports the reaction of the liquid sample with the oxygen containing carrier gas. In order to support the reaction of the liquid sample with the carrier gas, equally, a higher inner temperature of the reactor 5 could be set. The temperature of the reactor 5 can be set by means of a heating apparatus 13 surrounding the reactor 5. In the region of the insert 9 is located the reaction zone, in which during operation a temperature between 650° C. and 1300° C. rules. Optionally, within the reaction zone, in the insert 9, a bulk good (not shown) can be accommodated, which is retained by the sieve floor of the insert 9 provided with passageways 15. In contact with a surface in the interior of the reactor, for example, with the surface of the catalyst 11 or surfaces of the bulk good, the drops of the liquid sample heat up within a very short time, namely within a few tenths of a second, especially within less than 0.4 s, to the boiling-, or reaction temperature and are transformed into the gas phase.

Beneath the insert 9, there is arranged within the reactor 5 another chamber 17, in which during operation already a lower temperature rules than in the reaction zone. At the lower end of the reactor 5 (which is directed vertically during operation), opposite the drop cannula 3, is located a gas outlet 19, which opens into the interior of a filter unit 21, so that a gas mixture produced in the reactor 5 can flow via the passageways 15, the chamber 17 and the gas outlet 19 with the carrier gas into the filter unit 21. The filter unit 21 is connected with a condensing unit 25 via a gasline 23. The condensing unit 25 serves for the separation of water from the gas stream and is, therefore, in given cases, provided with a cooler, in order to accelerate the condensation of the water from the gas stream. The condensate is removed from the analytical apparatus 1 via line 27.

In the flow direction of the gas stream, behind the condensing unit 25, are arranged an optional drying unit 31, a further filter 33 and an analysis chamber 35. In analysis operation of the apparatus, in the analysis chamber 35, the content of reaction products of the analyte, for example, $CO_2$ and/or $NO_x$, contained in the gas stream is determined. As a rule, an infrared measuring arrangement, e.g. an infrared detector, is used for determining the $CO_2$ content. For determining the $NO_x$ content, as a rule, a chemiluminescence detector is applied. The measuring signals registered in the analysis chamber 35 are fed to a control unit 37 having a computer, for example, a microcontroller or microprocessor, which, based on the measuring signals, determines the concentration of the analyte in the sample metered into the reactor 5. Control unit 37 controls, moreover, also the metering system 2 for the metering of the liquid into the reactor 5. In such case, the analytical apparatus 1 can in analytical operation be operated according to the initially described, batch method or according to the likewise initially described, continuous measuring method.

The entire flow path of the carrier gas is sealed relative to the environment, so that no gas can exit from the analytical apparatus 1. The gas stream exits from the analytical apparatus 1 through a gas outlet (not shown) of the analysis chamber 37. The carrier gas can alternatively also, in a circulatory process of the analytical apparatus 1, be fed back via the gas supply 7. The components of the analytical apparatus 1 following the reactor 5 represent a flow resistance for the gas stream. In this way, it is possible to detect pressure changes in the interior of the reactor 5 even in the gas supply line 7, i.e. a pressure change effected, for example, by the transforming of a metered drop into the gas phase within the reactor 5 effects a pressure change correlated therewith in the gas supply line 7. A pressure measuring transducer 39 arranged in the gas supply line 7 registers the pressure reigning in the gas supply line 7 and provides an electrical signal (also referred to as the pressure signal) dependent, for example, proportionally dependent, on such pressure. From a sequence of such pressure signals, information concerning pressure changes in the reactor 5 can be developed, as explained in more detail below. The pressure measuring transducer 39 is connected on its output side with an input of the control unit 37, so that the pressure signals can be transmitted to the control unit 37. Since the entire carrier gas flow path is sealed relative to the environment, the pressure measuring transducer 39 can, for registering the pressure reigning within the reactor 5, basically be placed at any position along the flow path, for example, in the region of the gas outlet 19 or within the filter unit 21. Especially advantageously, however, the position is within the supply line 7, since there the temperature is still low, lying, for example, near room temperature.

A drop of a liquid sample metered via the drop cannula 3 into the reactor 5 transforms into the gas phase almost directly after entry into the reaction zone, especially by heat transfer from contact with a hot surface. If the liquid sample is an aqueous solution, which, besides water, also contains oxidizable components, then, for example, the contained water transforms by evaporation into gaseous $H_2O$, while the oxidizable components, such as, for example, organic carbon- or nitrogen containing compounds, react with the oxygen containing carrier gas to form gaseous oxides, such as $CO_2$ or $NO_x$. This makes itself noticeable within the reactor 5 by a pressure pulse, which is registerable by the pressure measuring transducer 39 arranged in the carrier gas supply line 7.

Figure 2:
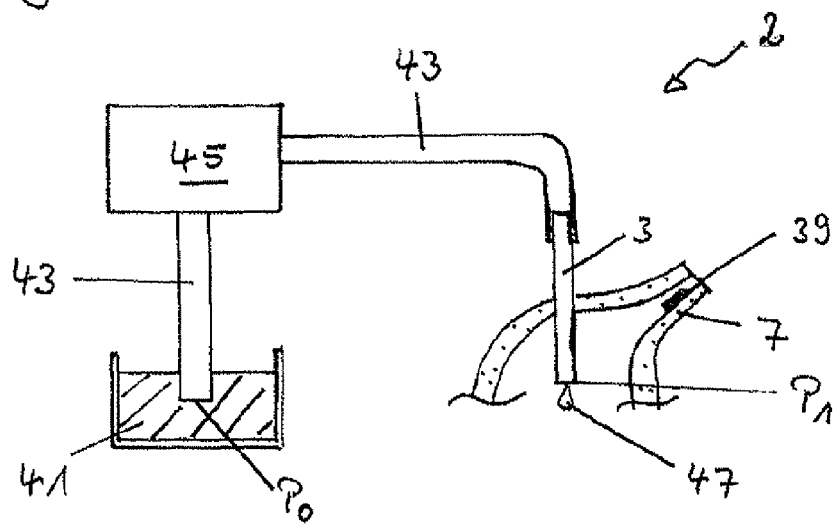
FIG. 2 is a schematic representation of the metering system of the analytical apparatus.

FIG. 2 shows the metering system 2 in more detail. From a source 41 sample liquid is fed via a supply line 43 by means of a pump 45. The pump 45 can be, for example, a peristaltic pump. In this case, the supply line 43 is in the form of a hose, preferably of an elastic material, such as e.g. silicone. The supply line can either extend into the reactor 5' or be connected, as shown in FIG. 2, in a manner sealed against escape of liquid at the joint, with a drop introduction cannula 3, which is preferably of a heat resistant material. The pump 45 is controlled via the control unit 37 (not shown in FIG. 2). In operation of the analytical apparatus, the pump is preferably controlled in such a manner that the sample liquid is metered in the form of individual drops 47 into the carrier gas supply line 7 and therewith into the reactor 5.

From time to time, for example, in regular intervals, the analytical apparatus 1 can be placed in maintenance operation offset. This can be initiated by the control unit 37.

In maintenance operation, the pressure signals output from the pressure measuring transducer 39 are evaluated by the control unit 37 as regards the instantaneous operating state of the analytical apparatus 1, especially the metering system 2. For example, the time interval elapsed since the last registered pressure pulse can be evaluated. If this time interval exceeds a stored threshold value, a signal can be generated, which triggers a warning report. In this way, a failure of the pump or plugging of the supply line can be detected early.

In maintenance operation, also a parameter more informative of the operating state of the metering system can be measured and output as a signal of the control unit 37, e.g. the time interval needed for supplying liquid from a first inlet side point $P_0$ of the supply line to the output $P_1$ of the supply line 43, or the drop introduction cannula 3 in the reactor 5 necessary. For this, the analytical apparatus is first placed in maintenance operation by having the pump 45 first move liquid still present in the supply line 43 back into the source 43. In such case, gas from the reactor 5 is pumped via the supply line 43 in the direction of the liquid supply 41. Gas leaving the supply line 43 into the liquid supply 41 is an indication that the supply line 41 is essentially free of liquid. In the source 43 or in the vicinity of the source 43, a suitable sensor can be provided, which detects the gas leaving into the source 43 and sends a corresponding signal to the control unit 37. Alternatively, a fixed time interval can be predetermined, over which the supplying of sample liquid from the supply line 43 and of gas from the reactor 5 into the source 41 should occur. This time interval can include some extra time in the manner of a safety factor so dimensioned that the supply line 43 after expiration of the time interval with safety factor is surely free of liquid.

In the next step, the control unit 37 issues to the pump 45 a signal, starting with which the pump 45 begins feeding a volume unit of sample liquid from the source 43 into the reactor 5. The time difference Δt between the beginning of feeding at the point in time $t_0$ and the registering of the first pressure pulse, which marks the transformation of the first metered drop into the gas phase, at the point in time $t_1$ is measured and processed by the control unit 37 as a signal representative of the instantaneous operating state of the metering system.

Figure 3:
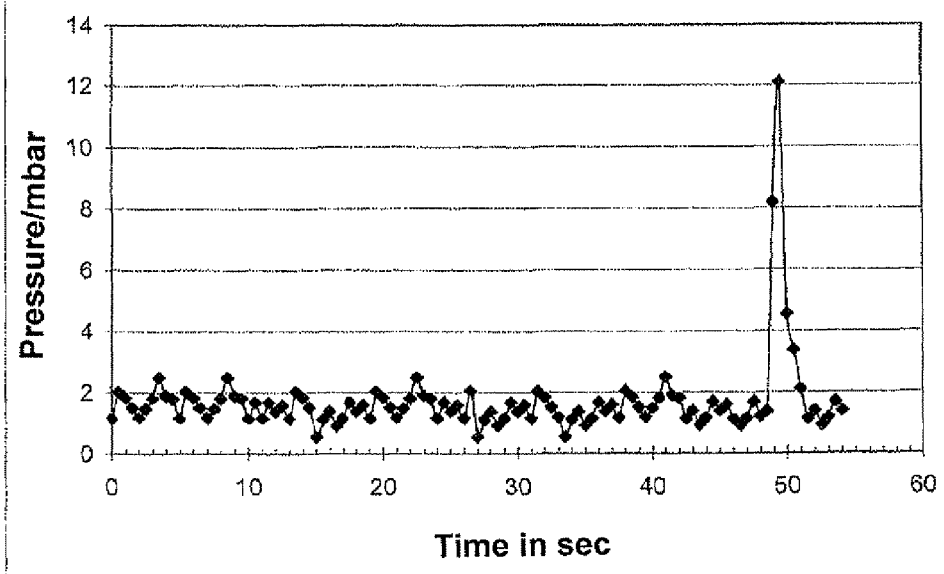
FIG. 3 is a pressure curve within the reactor of the analytical apparatus shown in FIG. 1, in the case of feeding a volume unit of a sample liquid from a source into the reactor.

FIG. 3 shows, by way of example, a sequence of pressure measured values, which were derived from a sequence of pressure signals output by the pressure measuring transducer 39 during the feeding a volume unit of sample liquid up to metering the first drop into the reactor 5. Measured on the abscissa of the graph is the time in s, while the ordinate shows the pressure in mbar. The points represent the individual pressure measurement values of the sequence. As can be seen from the curve of the sequence, there reigns in the reactor in the period of time between 0 and 48 s a relatively constant pressure between 0.5 and just under 3 mbar. After 49 s, there occurs a strong increasing of the pressure measurement values to a value of 12 mbar. After, for instance, 52 s is, the pressure has fallen back completely to values in the range between 1 and 2 mbar. This pressure pulse is attributed to the metering of a first drop into the reactor and its transformation into the gas phase.

Figure 4:
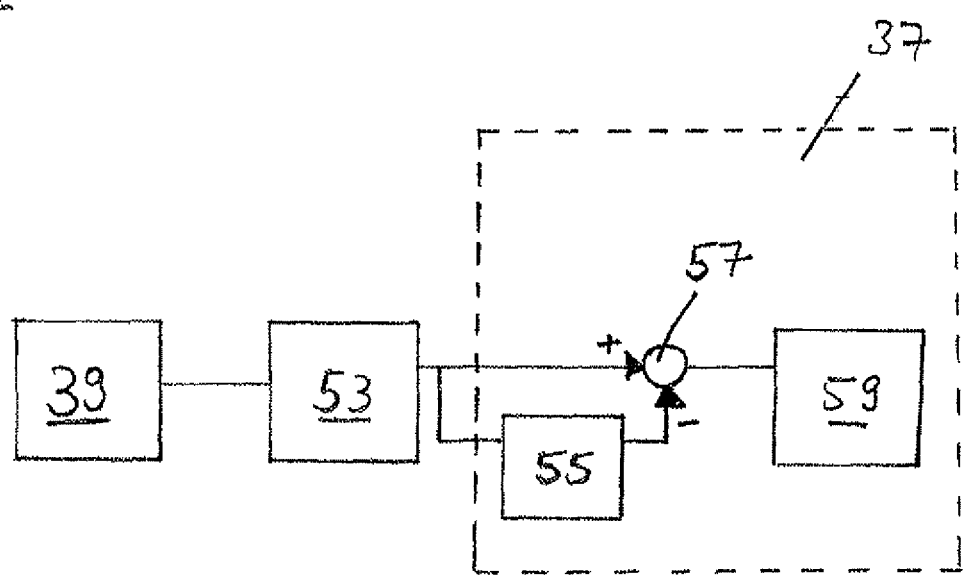
FIG. 4 is a schematic representation of the processing of the pressure signals.

Evaluation of the sequence of pressure signals of the pressure measuring transducer 39 occurs by means of the control unit 37 coupled with the pressure measuring transducer 39 in the manner described in the following (compare FIG. 4): The sensor signals transduced by the pressure measuring transducer 39 and, in given cases, amplified by an amplifier 53 are forwarded, in given cases, in digitized form, to the control unit 37. The in each case, last registered pressure signal $P_n$ is referred to in the following also as the current pressure signal. The control unit 37 includes an averaging unit 55, which forms a time average value at least of a certain number of the pressure signals of the sequence preceding the currently registered pressure signal $P_n$, for example, in the form of a sliding average value of all pressure signals registered within a predetermined time window. Equally, instead of a time window, also a certain number of pressure signals preceding the current pressure signal in the series could be predetermined. The forming of the sliding average value of at least a part of the pressure signals of the sequence preceding the current pressure signal $P_n$ is comparable to a digital low-pass filter. Correspondingly, also other comparable filter functions can be applied. The so obtained time average value forms a base pressure value $P_{average}$, which corresponds to a base pressure reigning in the reactor 5. The curve of the base pressure values versus time forms a type of "zero line" or "baseline" of the pressure reigning in the reactor 5. A ressure pulse due to a drop transforming into the gas phase leads to an increased pressure lying above this baseline.

The control unit 37 includes, furthermore, a subtracter 57, which is coupled on the input side with the pressure measuring transducer 39 and the averaging unit 55. The subtracter forms from the respective current sensor signal $P_a$ and the base pressure value $P_{average}$ a difference signal, which corresponds to a pressure change $P_{delta}$ between the currently registered pressure signal $P_n$ and the base pressure value $P_{average}$.

A threshold detector 59 is coupled on its input side with the output of the subtracter 57, so that the difference signal $P_{delta}$ of the subtracter 57 can be transmitted to the threshold detector 59. The threshold detector 59 compares the difference signal $P_{delta}$ with a predeterminable threshold value. If $P_{delta}$ lies above the predetermined threshold value, this is interpreted as a transformation of a drop of the sample liquid into the gas phase.

All here described means of the control unit 37 for registering a transformation of a volume unit of a sample liquid metered into the reactor 5 into the gas phase are preferably implemented as software of a microprocessor. They can, however, at least partially, also be implemented as electronic circuitry.

In the example of FIG. 3, the time difference between the beginning of feeding $t_0=0$ s and the first registered pressure pulse at the point in time $t_1=49$ s, in given cases, minus a time interval, which corresponds to the delay between the exit of the drop from the drop introduction cannula 3 and the registering of the pressure rise by the pressure measuring transducer 39, corresponds to the time interval required to feed a liquid volume, which corresponds to the internal volume of the supply line 43 between $P_0$ and $P_1$ plus the volume of the first metered drop, from the source 41 into the reactor 5.

Thus, in the case of known internal volume of the supply line 43, for example, known from an earlier measurement, and known drop volume, for example, known from a calibration, based on the so ascertained time difference Δt, the feed rate R of the metering system 2 can be expressed according to the following relationship $$R = \frac{V_T}{\Delta t} \text{ with } V_T = V_I + V_D \qquad (1)$$

wherein $V_T$ is the total volume composed of the internal volume $V_I$ of the supply line 43 and the volume of the drop of the sample liquid $V_D$.

On the other hand, in the case of known feed rate R of the metering system, the same relationship can also be used to determine volume supplied within a time Δt.

Over the duration of operation of the analytical apparatus 1, or the metering system 2, especially also in the case of the embodying of the metering system 2 as a peristaltic pump over the duration of operation of an individual hose, at regular intervals, the time interval Δt necessary between beginning of feeding and the metering of the first liquid drop can be determined and stored in a memory of the control unit 37. From a plurality of stored values Δt or values derived therefrom, a trend can be ascertained and evaluated.

The trend can be taken into consideration for diagnosis of the metering system 2. This is presented in the following in more detail based on the example of a peristaltic pump. When, from a diagnostic result, a maintenance measure, such as e.g.

the cleaning or exchange of parts of the metering system 2, e.g. the hose a peristaltic pump, is indicated, it can be sensible, after performing the maintenance measure, to effect a reset, e.g. only $\Delta t$-values, or values derived therefrom, registered since the maintenance measure are taken into consideration for ascertaining a (new) trend.

FIG. 5A shows a first example of a curve for feed rate $R_A$ in µl/min derived from $\Delta t$ based on Equation (1) versus duration of operation of an elastic hose of a peristaltic pump. Over the duration of operation, feed rate $R_A$ is decreasing. The compressive stroking movement of the peristaltic pump leads to decreasing elasticity and thus an always smaller liquid volume transported per individual compressive stroking. This leads to the observed decrease of the feed rate $R_A$.

FIG. 5B shows a second example of a curve for feed rate $R_B$ in µl/min derived from $\Delta t$ based on Equation (1) versus duration of operation of an elastic hose of a peristaltic pump. Over the duration of operation, there is first, as in the example of FIG. 5A, a decrease of the feed rate $R_B$. After, for instance, 3 days, however, an increase of the feed rate $R_B$ is to be seen. This is attributed as follows: Due to entrained particles in the sample liquid or biological growth on the inner wall of the hose, the internal volume $V_T$ of the hose lessened. This leads to the fact that $\Delta t$ decreases, since the peristaltic pumps a smaller liquid volume feed to achieve at the position P1 (FIG. 2) a first drop, which is metered into the reactor 5 and detected. Since in the determining of $R_B$ from Equation (1), however, a constant volume $V_T$ is applied, the feed rate $R_B$ derived from $\Delta t$ correspondingly rises with the really lessening internal volume of the hose.

The liquid volume actually supplied by the peristaltic pump by compressive stroking movements per unit time decreases with time, however, due to the aging of the hose, which leads to a loss of elasticity and therewith to a lessening of the restoring force of the hose. This effect dominates in the example of FIG. 5B first in the curve for the feed rate $R_B$ derived from $\Delta t$. After 3 days, however, the influence the decrease of the hose internal volume predominates, which leads to a rise of $R_B$.

From these examples, it can be seen that the trend of $\Delta t$, or values derived therefrom, such as the feed rate R according to Equation (1), over the duration of operation of the metering system can provide information concerning which is the dominating influence that can lead to defective meterings. Thus, the curve of $R_B$ in FIG. 5B is characteristic for a volume decrease in the hose and suggests biological growth on the hose inner wall or solid entrained particles in the sample liquid.

Furthermore, the trend can be evaluated for predicting when maintenance, for example, exchange of the hose or a cleaning of the hose, will be required. For example, there can be stored in the control unit a library of experientially based models, which describe for different disturbing influences, such as aging of the hose material or biological growth, the curve of $\Delta t$ or a value derived therefrom. By matching the appropriate model to the ascertained data and extrapolation, a point in time for the next maintenance measure can be ascertained. Alternatively, also upper and lower threshold values can be furnished for $\Delta t$, or a value derived therefrom, in the case of whose exceeding, or subceeding, an alarm is output, which triggers a maintenance measure.

Furthermore, based on the time difference $\Delta t$, and especially taking into consideration the trend of the $\Delta t$-values, an adjusting of the analytical apparatus can be performed. For example, for the case, in which, as in the case of FIG. 5A, the decreasing of the elasticity of the hose of a peristaltic pump is the dominating influence on the accuracy of measurement, a correction factor can be determined for the volume metered into the reactor in the case of equally remaining metering time and feed velocity of the peristaltic pump, i.e. velocity of its compressive stroking movements. In analytical operation, in batch operation, or in continuous operation, the analytical result is treated with the ascertained correction factor and so a high accuracy of the analytical result is achieved by correct determining of the actually metered volume.

Alternatively, also the feed velocity of the peristaltic pump can be adjusted or controlled in such a manner that the feed rate $R_A$ returns to its original value, or to another desired value. In this way, by variation of the feed velocity of the peristaltic pump and/or the metering time, the applied sample volume used per analysis in the case of batch operation, or the feed rate in the case of continuous operation, can be set precisely.

The invention claimed is:

1. A method for operating an analytical apparatus for determining the concentration of an analyte, especially an oxidizable substance, in a sample liquid, comprises the steps of:
    placing the analytical apparatus in a maintenance operation mode;
    operating a metering system, which includes a pump, especially a peristaltic pump, and a supply line for metering volume units of a sample liquid from a source via the supply line into a reactor, the temperature inside the reactor being higher than the boiling temperature of the sample liquid, so that said volume units of the sample liquid metered into the reactor transform into the gas phase following entry into the reactor and a carrier gas in flowing through the reactor;
    registering at least one measuring transducer signal for detecting the transforming of the volume unit of the sample liquid into the gas phase; and
    deriving, with application of the measuring transducer signal a signal correlated with an instantaneous operating state of the metering system, and
    said signal correlated with an instantaneous operating state of the metering system is a status signal, or
    said signal correlated with an instantaneous operating state of the metering system has a signal value, from which a feeding capacity of the metering system or liquid volume supplied in a certain unit of time can be derived, or
    said signal correlated with an instantaneous operating state of the metering system is a signal representing a time span required for transporting sample liquid from the source into the reactor or value derived therefrom, or
    said signal correlated with an instantaneous operating state of the metering system is a signal representing a feed rate of the metering system.

2. The method as claimed in claim 1, wherein:
    the analytical apparatus over the duration of operation of the metering system is, placed repeatedly in time intervals, from an analytical operation mode to the maintenance operation mode; and
    the signal correlated with the instantaneous operating state is ascertained and stored in a memory.

3. The method as claimed in claim 1, further comprising the steps of:
    registering a first point in time, at which operation of the metering system is begun for metering volume units of the sample liquid into the reactor;
    registering a second point in time, at which the transformation of a volume unit of the sample liquid metered into the reactor is detected based on the measuring transducer signal; and determining the time difference between the first and second points in time as the signal correlated with the instantaneous operating state of the metering system.

4. The method as claimed in claim 3, wherein:
the placing of the analytical apparatus into the maintenance operation mode includes a step of removing sample liquid from the supply line, especially by having the pump feed sample liquid from the supply line back into the source until gas escapes from the supply line into the source.

5. The method as claimed in claim 3, wherein:
as a second point that point is registered, for the first time after the first point in time, a transformation of a volume unit metered into the reactor into the gas phase is detected.

6. The method as claimed in claim 1, wherein:
the measuring transducer signal is a pressure signal of a pressure measuring transducer.

7. The method as claimed in claim 6, wherein:
for detection of the transformation of a volume unit metered into the reactor, a sequence of pressure signals is registered, which are correlated with pressure reigning in the reactor.

8. The method as claimed in claim 7, wherein:
a current pressure signal of the sequence is compared with a base value of the pressure in order to ascertain a pressure change, and said pressure change is compared with a predetermined threshold value, and based on a result of the comparison, it is registered, whether the pressure change corresponds to a pressure pulse effected by transformation into the gas phase of a volume unit metered into the reactor.

9. The method as claimed in claim 8, wherein:
the base value of the pressure is formed by average formation, especially by sliding average formation using at least two pressure signals preceding the current pressure signal in the series of pressure signals.

10. The method as claimed in claim 8, wherein:
it is registered to that the pressure change corresponds to a pressure pulse effected by transformation into the gas phase of a volume unit, especially a drop, metered into the reactor is registered when the pressure change exceeds the predetermined threshold value.

11. The method as claimed in claim 1, wherein:
over the duration of operation of the metering system, a trend of the stored signals, especially the time differences, correlated with the operating state of the metering system is determined and evaluated.

12. The method as claimed in claim 11, wherein:
a point in time for maintenance measures, especially for cleaning or for replacement of the supply line, is derived from the trend.

13. The method as claimed in claim 3, wherein:
an adjusting of the analytical apparatus is performed based on the signal, especially the time difference, correlated with the operating state of the metering system.

14. The method as claimed in claim 13, wherein:
the trend of the time differences ascertained in the course of the duration of operation of the analytical apparatus or the metering system is taken into consideration in adjusting the analytical apparatus.

15. The method as claimed in claim 2, wherein:
the signal, especially the time difference, correlated with the operating state of the metering system is used for controlling the metering system.

16. A method for operating an analytical apparatus for determining the concentration of an analyte, especially an oxidizable substance, in a sample liquid, comprises the steps of:
placing the analytical apparatus in a maintenance operation mode;
operating a metering system, which includes a pump, especially a peristaltic pump, and
a supply line, for metering volume unit of a sample liquid from a source via the supply line into a reactor, the temperature inside the reactor being higher than the boiling temperature of the sample liquid, so that said volume units of the sample liquid metered into the reactor transforms into the gas phase following entry into the reactor and a carrier gas is flowing through the reactor;
registering at least one measuring transducer signal for detecting the transforming of the volume units of the sample liquid into the gas phase; and
deriving, with application of the measuring transducer signal, a signal representing an instantaneous operating state of the metering system.

17. The method according to claim 16, said signal representing an instantaneous operating state of the metering system is a status signal, or
said signal representing an instantaneous operating state of the metering system has a signal value, from which a feeding capacity of the metering system or liquid volume supplied in a certain unit of time can be derived, or
said signal representing a time span required to transporting sample liquid from the source into the reactor or a value derived therefrom, or
said signal representing an instantaneous operating state of the metering system is a signal representing a feed rate of the metering system.

18. The method according to claim 16, said signal representing an instantaneous operating state of the metering system being a time interval required for feeding a volume unit of the sample liquid, especially a droplet of said sample liquid, from the source into the reactor.

19. The method according to claim 18, comprising the steps:
moving liquid present in the supply line back into the source;
feeding a volume unit of sample liquid from the source into the reactor; registering a first pressure pulse, which marks the transformation to the gas phase of a first drop of the sample liquid metered into the reactor;
determining the time difference between the point in time of beginning of feeding said volume unit of sample liquid from the source into the reactor and the point in time at which said first pressure pulse is registered as the signal representative of the instantaneous operating state of the metering system.

* * * * *